US007527719B2

(12) United States Patent
Liu et al.

(10) Patent No.: US 7,527,719 B2
(45) Date of Patent: May 5, 2009

(54) CAPILLARY ELECTROPHORESIS CHIP APPARATUS FOR DETECTING NUCLEOTIDE POLYMORPHISM AND SINGLE NUCLEOTIDE POLYMORPHISM

(75) Inventors: Peng Liu, Beijing (CN); Wanli Xing, Beijing (CN); Dong Liang, Beijing (CN); Jing Cheng, Beijing (CN)

(73) Assignees: Capitalbio Corporation, Beijing (CN); Tsinghua University, Beijing (CN)

( * ) Notice: Subject to any disclaimer, the term of this patent is extended or adjusted under 35 U.S.C. 154(b) by 556 days.

(21) Appl. No.: 10/500,180

(22) PCT Filed: Nov. 29, 2002

(86) PCT No.: PCT/CN02/00857

§ 371 (c)(1),
(2), (4) Date: Mar. 23, 2005

(87) PCT Pub. No.: WO03/058227

PCT Pub. Date: Jul. 17, 2003

(65) Prior Publication Data

US 2005/0161335 A1 Jul. 28, 2005

(30) Foreign Application Priority Data

Nov. 30, 2001 (CN) .............................. 01 1 39831

(51) Int. Cl.
*G01N 27/453* (2006.01)
(52) U.S. Cl. ..................................... 204/602; 204/601
(58) Field of Classification Search ......... 204/450–470, 204/600–621; 422/100
See application file for complete search history.

(56) References Cited

U.S. PATENT DOCUMENTS 3,502,558 A * 3/1970 Hodes ........................ 204/499
6,939,451 B2 * 9/2005 Zhao et al. .................. 204/451

FOREIGN PATENT DOCUMENTS

| CN | 1168720 | 12/1997 |
|---|---|---|
| CN | 1235674 | 11/1999 |
| CN | 1320818 | 11/2001 |
| EP | 0 770 871 | 5/1997 |
| JP | 8233778 | 9/1996 |
| JP | 2000227414 | 8/2000 |
| WO | WO 00/58721 | 10/2000 |
| WO | WO 01/68898 | 9/2001 |

OTHER PUBLICATIONS

Supplementary European Search Report for EP 02782653.6, mailed Aug. 9, 2007, 3 pages.
International Search Report for PCT/CN02/00857, mailed on May 15, 2003, 3 pages.

* cited by examiner

*Primary Examiner*—Alexander Noguerola
*Assistant Examiner*—Hosein Kafimosavi
(74) *Attorney, Agent, or Firm*—Morrison & Foerster LLP

(57) ABSTRACT

The present invention provides a capillary electrophoresis chip apparatus for detecting nucleotide polymorphism or single nucleotide polymorphism belonging to capillary electrophoresis apparatuses. The apparatus comprises an upper channel layer comprising a one-, two-, or multi-dimensional microfluid channel and an electrode aperture structure for loading sample, a middle electrode layer for sealing the microfluid channel to form an intact capillary and providing the needed voltage for electrophoresis; and a lower heating layer for providing a stable temperature gradient for electrophoresis. The upper, middle and lower layers are thermal conductive and adhesive to each other.

19 Claims, 4 Drawing Sheets

CAPILLARY ELECTROPHORESIS CHIP APPARATUS FOR DETECTING NUCLEOTIDE POLYMORPHISM AND SINGLE NUCLEOTIDE POLYMORPHISM

CROSS-REFERENCE TO RELATED APPLICATIONS

This application is the national phase of PCT application PCT/CN2002/000857 having an international filing date of Nov. 29, 2002, which claims priority from China application number 01139831.0 filed Nov. 30, 2001. The contents of these documents are incorporated herein by reference.

TECHNOLOGY FIELD OF INVENTION

The present invention relates to a capillary electrophoresis chip apparatus for detecting single nucleotide polymorphism (SNP). The invention is in the technology filed of capillary electrophoresis chip apparatus.

BACKGROUND OF THE INVENTION

Single Nucleotide Polymorphism (SNP) exists universally in the genome. It was estimated that there are about three million SNP sites in the human genome. The large number of SNP sites in the genome, combined with its spectral-density and dimorphism, makes SNP an ideal candidate as a third-generation genetic marker. Identification and study of SNP sites is one of the important goals and aspects of the human genome project. As a polymorphic marker, SNP finds significant application in the areas of anthropology, medical diagnosis, disease research, environment-sensitive factor study, drug screening, and forensic evaluation. Direct DNA sequencing is the most straight-forward method for detecting SNP, but this method is both laborious and inefficient. Recent studies have focused more on high throughput methods. One type of high throughput detection method, based on the DNA denaturation dynamics, includes gradient denaturing gel electrophoresis, fixed-concentration denaturing electrophoresis, capillary denaturing electrophoresis, and denaturing high performance liquid chromatography. These methods, however, all require addition of denaturants. The mechanism through which the denaturants affect electrophoresis and chromatography is complex. Furthermore, the selection of denaturants, the choice of electrophoresis or chromatography conditions, as well as the establishment of gradients, all pose significant technical difficulties.

DETAILED DESCRIPTION OF THE INVENTION

The purpose of the present invention is to provide a fast, efficient, and sample-saving capillary electrophoresis chip apparatus for detecting nucleotide polymorphism and single nucleotide polymorphism that uses temperature to replace denaturants.

The present invention is directed to a capillary electrophoresis chip apparatus comprising an upper channel layer comprising a microfluid channel and an electrode aperture for loading samples and applying electrodes; a middle electrode layer for sealing the microfluid channel to form an intact capillary and providing the needed voltage for the electrophoresis chip; and a lower heating layer for providing a stable temperature gradient for electrophoresis. The upper, middle, and lower layers are thermal conductive and adhesive to each other.

The microfluid channel described herein can be one dimensional, two dimensional, or any kind of multidimensional channel. The sectional width or diameter of the microfluid channel is between 5 to 200 µm; the depth of the fluid channel is between 5 to 200 µm; and the length of the electrophoresis separation channel is between 1 to 30 cm. The material for making the middle electrode layer can be gold, platinum, or graphite. The upper surface of the middle electrode layer can be coated with a layer of polydimethylsiloxane (PDMS). The heating layer described herein may comprise two or more sets of temperature control elements that are spaced apart, each being kept at a different constant temperature so as to form a stable spatial temperature gradient. The temperature gradient described herein can also be a temporal temperature gradient formed by gradually and uniformly heating the whole chip.

Proof of use: desired objects were achieved.

EXAMPLE

Figure 1:
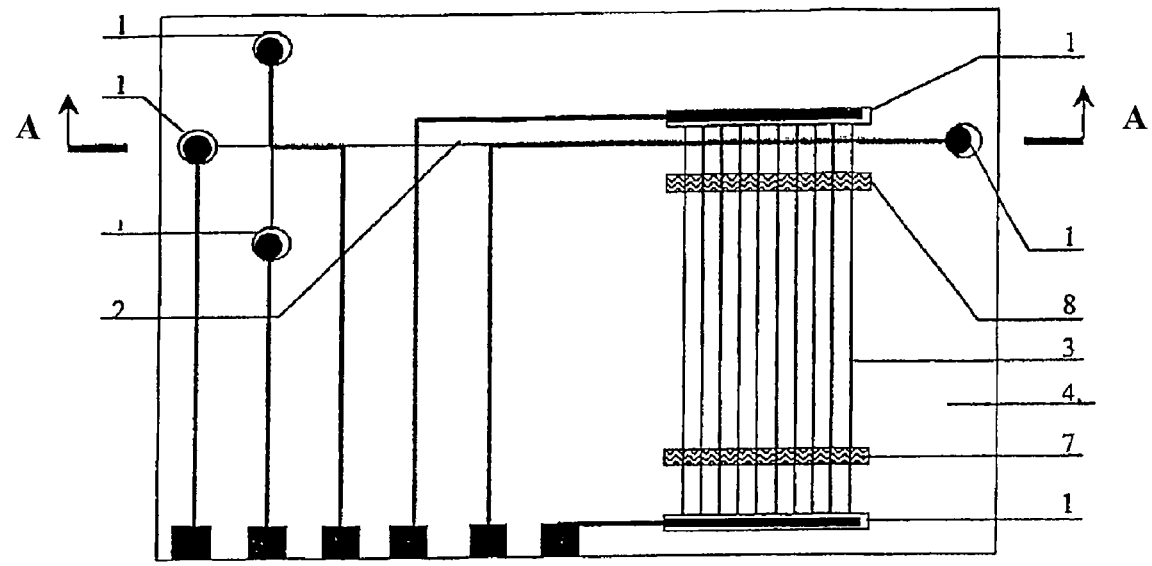
FIG. 1 provides a schematic diagram of a capillary electrophoresis chip apparatus of the present invention for detecting nucleotide polymorphism and single nucleotide polymorphism.
Figure 2:
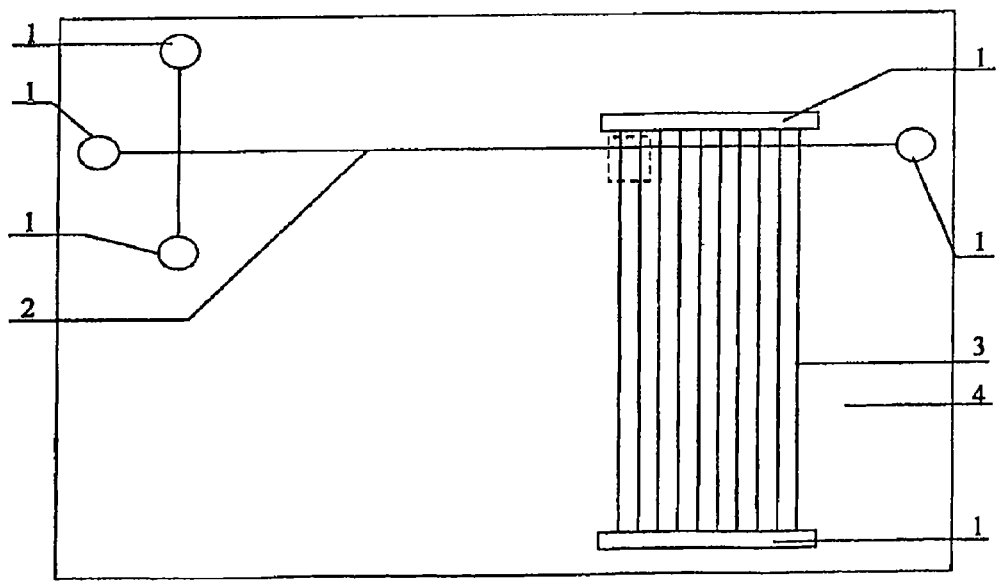
FIG. 2 provides a top view of an upper microfluid channel layer of a preferred apparatus of the present invention for detecting nucleotide polymorphism and single nucleotide polymorphism.
Figure 3:
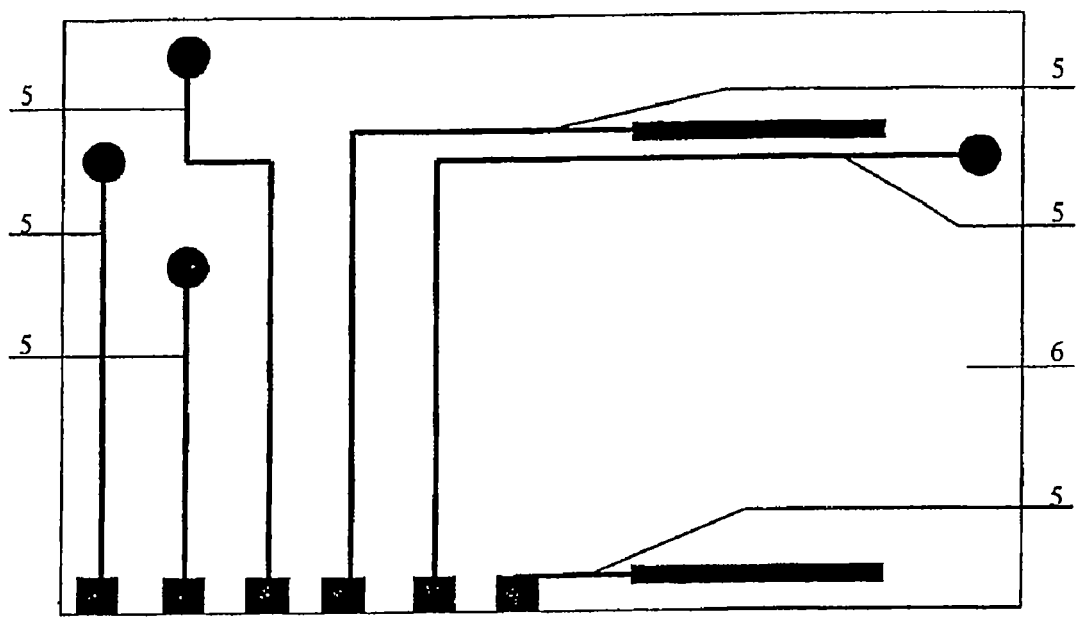
FIG. 3 provides a top view of a middle electrode layer of a preferred apparatus of the present invention for detecting nucleotide polymorphism and single nucleotide polymorphism.
Figure 4:
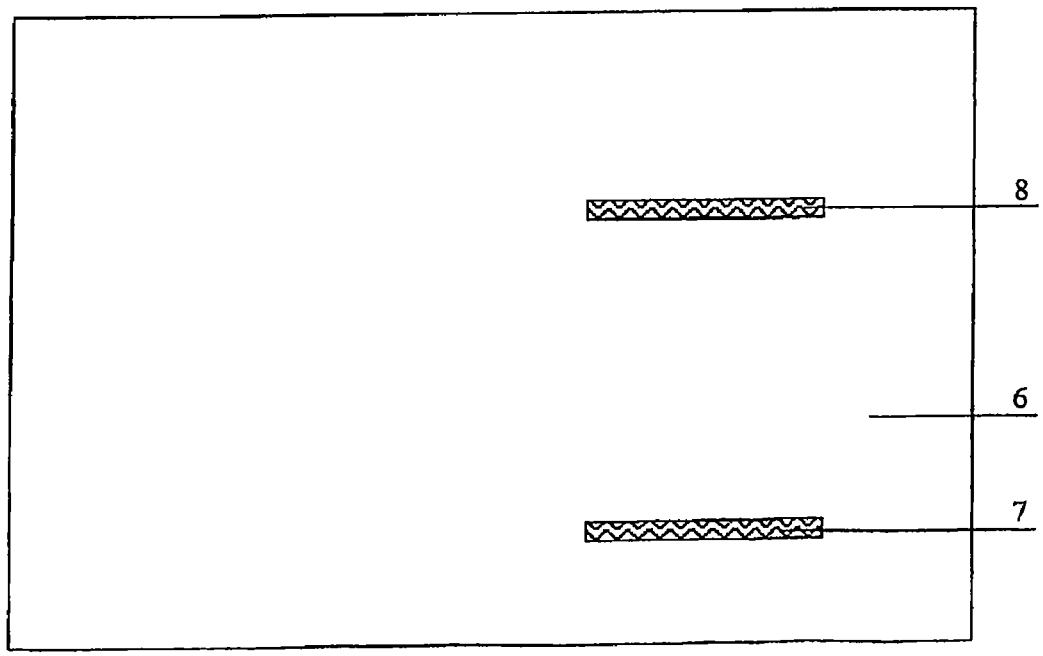
FIG. 4 provides a top view of a lower heating layer of a preferred apparatus of the present invention for detecting nucleotide polymorphism and single nucleotide polymorphism.
Figure 6:
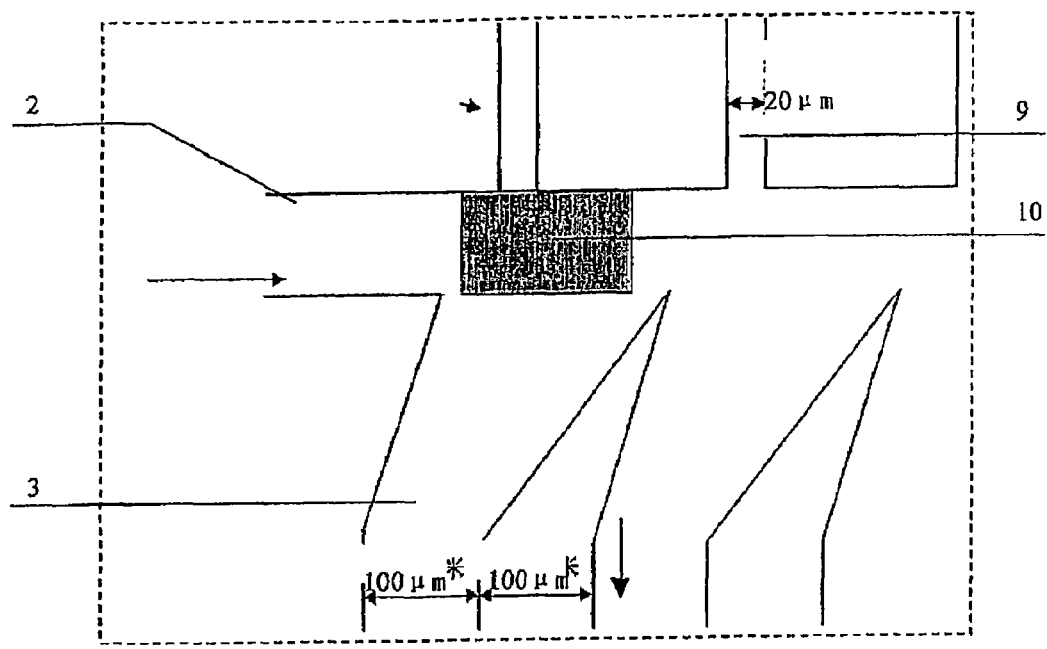
FIG. 6 provides a magnified top view of the box with dotted lines shown in FIG. 2.
Figure 5:
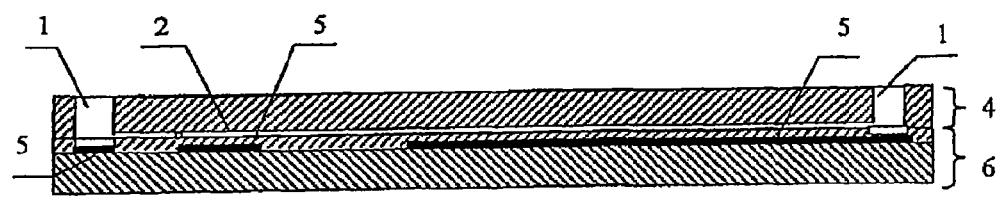
FIG. 5 provides a longitudinal view (A-A direction) of a preferred apparatus as shown in FIG. 1 for detecting nucleotide polymorphism and single nucleotide polymorphism.

See FIGS. 1-6. FIG. 1 is a schematic diagram showing the overlay of the upper and lower layers shown in FIGS. 2 and 3. 1 refers to electrode aperture. 2 refers to first-dimension electrophoresis channel. 3 refers to second-dimension electrophoresis channels. There are total of 50 second-dimension electrophoresis channels. Each channel has a width of 100 µm and a depth of 10 µm, and is 100 µm apart from each other. The total length of the electrophoresis channels is 30 cm. The connecting channels between the electrophoresis channels and the electrode apertures are about 20 µm wide. 4 refers to an upper fluid channel layer, i.e., the channel layer. In a preferred apparatus, channel layer 4 is made of polydimethylsiloxane (PDMS), or any one of silicone rubber, plastic, quartz, or glass. The microfabrication methods for making the electrophoresis channels and electrode apertures 1 for loading samples includes casting, molding, etching, and lithography, depending on the material used for the channel layer. The cross-section of the electrophoresis channels (i.e., the microfluid channels) on channel layer 4 can be rectangular, or of any other geometrical shapes. The electrophoresis channels described above are open capillary channels, which can be sealed into complete capillaries by a cover slip. Similarly, the fluid channels connected to the electrophoresis channels also need to be sealed by cover slips to form a complete fluid container. 5 refers to electrodes on middle electrode layer 6. Middle electrode layer 6 can be used to seal the upper electrophoresis separation channels to form a complete capillary. It also contains electrodes that provide the needed voltage for electrophoresis. As shown in FIG. 1, the exposed portions on electrodes 5 are in direct contact with the solution in the electrode separation channels only in places where contact is necessary. Electrodes 5 provide the required voltage, which can be changed by computer programs. Electrode layer 6 can be formed by depositing metal on the surface of a glass followed by etching. The electrode layer can be made of any one of gold, platinum, or graphite. An insulation layer can be formed on the top of the electrode layer by oxidizing method, leaving exposed metal only in places that correspond to electrode apertures 1 on channel layer 4. Alternatively, an insulation layer can be formed by directly coating the electrode layer with a layer of PDMS, leaving exposed metal only in places that correspond to electrode apertures 1. When channel layer 4 and electrode layer 6 are adhered to each other, the solution in electrode apertures 1 are in direct contact with the exposed electrodes at the bottom of the apertures on electrode layer 6. These exposed electrodes provide the required voltage for electrophoresis. Electrodes 5 can also be needle-like structures, which can be inserted into electrode apertures 1 on channel layer 4. The inserted electrodes are thus in contact with the solution, and exert their functions in electrophoresis. The heating layer contains two sets of temperature control elements, one for heating and the other for cooling. Heating element 7 is kept at a relatively high constant temperature, while cooling element 8 is kept at a relatively low constant temperature. Heat is transmitted from the heating element to the cooling element across the glass at the bottom of electrode layer 6. As a consequence, a stable spatial temperature gradient within the glass can be achieved. The heating and cooling elements in the present example can be semiconductive temperature control elements, or can be electric resistant elements. FIG. 6 provides a magnified top view of the box with dotted lines shown in FIG. 2. 9 refers to the channels connected to electrode apertures 1, with a width of 20 μm. 10 refers to the sample being analyzed. 2 refers to the first-dimension electrophoresis channel, 3 refers to the second-dimension electrophoresis channels. The arrows represent the directions of corresponding electrophoresis. During the first-dimension electrophoresis, sample 10 can be prevented from diffusing into second-dimension electrophoresis channels 3. During the second-dimension electrophoresis, second-dimension electrophoresis channels 3 and channels 9 that connect to electrode apertures 1 can be prevented from interfering with the first-dimension electrophoresis process. Furthermore, bands formed during the first-dimension electrophoresis are kept intact as they enter second dimension electrophoresis channels 3, and do not diffuse into other neighboring channels. FIG. 5 provides a longitudinal view of FIG. 1 (A-A direction). The structure is the same as described above.

Figure 7:
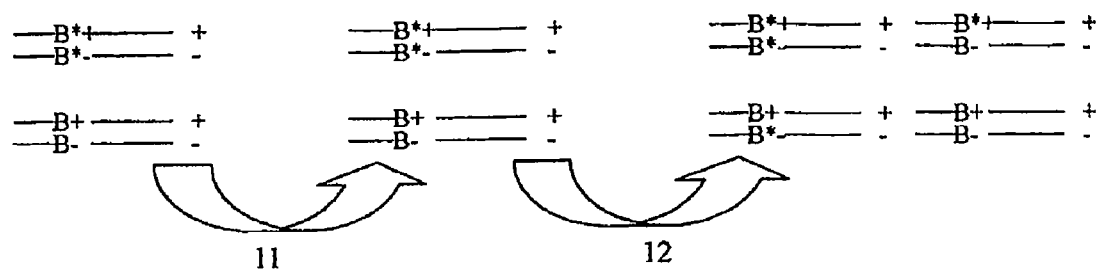
FIG. 7 provides a schematic diagram of the pretreatment process of the sample used for the preferred apparatus of the present invention.

FIG. 7 provides a schematic diagram of the pre-treatment process of samples used for the preferred apparatus of the present invention. 11 refers to a PCR polymerization reaction process, and 12 refers to a denaturation and renaturation process. In this figure, B represents any base of AGCT; B* represents a SNP site; "+" and "−" are used to differentiate the two chains of a DNA. FIG. 7 depicts the situation where an SNP site exists. Thus, four different kinds of DNA fragments of the same lengths are obtained, some of which contain mismatches. If no SNP exists, there is one kind of DNA fragments. The sections below further illustrate the process of detecting SNP of the present invention in conjunction with FIG. 7. A sample suspected of containing SNP sites is pre-treated to allow formation of mismatches at the SNP sites. See FIG. 7. Restriction fragments of different lengths are then separated during the first-dimension electrophoresis. The DNA fragment that contains an SNP appears in the same band as other DNA fragments of the same length. During the first dimension electrophoresis, electrical voltage is applied to the two ends of the second dimension channels, thereby preventing sample from diffusing into second-dimension electrophoresis channels 3. Second-dimension electrophoresis channels are a row of parallel channels. Each band resulting from the first-dimension electrophoresis enters the second-dimension row of electrophoresis channels 3 under the control of electrical voltage for further electrophoresis. During electrophoresis, the heating layer provides a gradually increasing temperature gradient at the direction of second-dimension electrophoresis. DNA fragments with mismatches have a lower denaturation temperature than those without mismatches, and thus denature first as electrophoresis proceeds toward regions of higher temperature. Because denatured DNA fragments encounter greater retardation, they become separated from non-denatured DNA fragments of the same length. As long as the resolution of the system is sufficiently high, denatured DNA fragments can be separated from non-denatured DNA fragments of the same length. Accordingly, if only a single band appears as a result of the second-dimension electrophoresis, it can be concluded that there is no SNP site on the DNA fragment. Alternatively, if more than one bands appear as a result of the second-dimension electrophoresis, it can be concluded that there is at least one SNP site on the DNA fragment. Analysis of the data obtained above further indicates which DNA restriction fragments harbor SNP site(s).

The temperature gradient described above can also be a temporal temperature gradient. During the second-dimension electrophoresis, the electrophoresis chip can be uniformly heated. The same purpose as described above can be achieved by heating the electrophoresis chip at a properly controlled rate during the second dimension electrophoresis. If the separation channel is sufficiently long, and the electrophoresis separation efficiency is sufficiently high, a single-dimension ordinary capillary can also be used. The DNA fragments of different lengths are first separated during electrophoresis without a temperature gradient, and then further electrophoresis can proceed under a temporal temperature gradient.

As shown above, the present invention takes advantage of the high speed, high efficiency, and low sample consumption characteristics of capillary electrophoresis technology, and avoids the use of denaturants in the mean time. The detection process is easy to control, and the gradient is easy to achieve.

INDUSTRIAL APPLICATION

The capillary electrophoresis chip apparatus of the present invention can find broad applications in detecting nucleotide polymorphism and single nucleotide polymorphism.

We claim:

1. A capillary electrophoresis chip apparatus for detecting a nucleotide polymorphism or a single nucleotide polymorphism, said apparatus comprising an electrophoresis chip comprising:

an upper channel layer, comprising a first-dimension microfluidic channel, a plurality of second-dimension microfluidic channels in fluid communication with the first-dimension microfluidic channel, and two or more sets of electrode apertures in fluid communication with the first-dimension microfluidic channel and with the plurality of second-dimension microfluidic channels;

a middle electrode layer capable of sealing the first-dimension microfluidic channel and the plurality of second-dimension microfluidic channels to form intact capillaries, said middle electrode layer comprising electrodes capable of providing a needed voltage along the first-dimension microfluidic channel and along the plurality of second-dimension microfluidic channels; and a lower heating layer capable of providing a stable temperature gradient for electrophoresis along the plurality of second-dimension microfluidic channels, said lower heating layer comprising two or more sets of temperature control elements that are spaced apart from each other and positioned approximately perpendicular to the plurality of second-dimension microfluidic channels, wherein the upper channel layer, the middle electrode layer, and the lower heating layer are thermally conductive and adhesive to each other, and the capillary electrophoresis chip apparatus is capable of detecting a nucleotide polymorphism or a single nucleotide polymorphism.

2. The capillary electrophoresis chip apparatus of claim 1, wherein the sectional width or diameter of the first-dimension microfluidic channel and the plurality of second-dimension microfluidic channels is between 5 to 200 µm; the depth of the first-dimension microfluidic channel and the plurality of second-dimension microfluidic channels is between 5 to 200 µm; and the total length of the first-dimension microfluidic channel and the plurality of second-dimension microfluidic channels is between 1 to 30 cm.

3. The capillary electrophoresis chip apparatus of claim 1, wherein the middle electrode layer is made of gold, platinum, or graphite.

4. The capillary electrophoresis chip apparatus of claim 1, wherein the middle electrode layer is coated with a layer of polydimethylsiloxane (PDMS).

5. The capillary electrophoresis chip apparatus of claim 1, wherein each temperature control element is kept at a different constant temperature so as to form a spatial temperature gradient.

6. The capillary electrophoresis chip apparatus of claim 1, wherein the stable temperature gradient is a temporal temperature gradient established by gradually and uniformly heating the whole chip.

7. The capillary electrophoresis chip apparatus of claim 1, wherein the upper channel layer comprises a first-dimension microfluidic channel and a plurality of second-dimension microfluidic channels in fluid communication with the first-dimension microfluidic channel, and the lower heating layer comprises two sets of temperature control elements that are spaced apart from each other and positioned underneath the plurality of second-dimension microfluidic channels, wherein each temperature control element is kept at a different constant temperature so as to form a spatial temperature gradient.

8. The capillary electrophoresis chip apparatus of claim 1, wherein the sectional width or diameter of the first-dimension microfluidic channel and the plurality of second-dimension microfluidic channels ranges from 5 to 200 µm.

9. The capillary electrophoresis chip apparatus of claim 1, wherein the first-dimension microfluidic channel has a sectional width or diameter of 100 µm.

10. The capillary electrophoresis chip apparatus of claim 1, wherein each of the plurality of second-dimension microfluidic channels has a sectional width or diameter of 100 µm.

11. The capillary electrophoresis chip apparatus of claim 1, wherein the depth of the first-dimension microfluidic channel and the plurality of second-dimension microfluidic channels ranges from 5 to 200 µm.

12. The capillary electrophoresis chip apparatus of claim 1, wherein the first-dimension microfluidic channel has a depth of 10 µm.

13. The capillary electrophoresis chip apparatus of claim 1, wherein each of the plurality of second-dimension microfluidic channels has a depth of 10 µm.

14. The capillary electrophoresis chip apparatus of claim 1, wherein the total length of the first-dimension microfluidic channel and the plurality of second-dimension microfluidic channels ranges from 1 to 30 cm.

15. The capillary electrophoresis chip apparatus of claim 1, wherein the total length of the first-dimension microfluidic channel and the plurality of second-dimension microfluidic channels is 30 cm.

16. The capillary electrophoresis chip apparatus of claim 1, wherein the upper channel layer comprises 50 second-dimension microfluidic channels.

17. The capillary electrophoresis chip apparatus of claim 1, wherein the plurality of second-dimension microfluidic channels are spaced 100 µm from each other.

18. The capillary electrophoresis chip apparatus of claim 1, wherein the upper channel layer further comprises a plurality of connecting channels in fluid communication with the plurality of second-dimension microfluidic channels and with the electrode apertures.

19. The capillary electrophoresis chip apparatus of claim 18, wherein each of the plurality of connecting channels has a width of 20 µm.

* * * * *